(12) United States Patent
Nazeri

(10) Patent No.: US 9,603,689 B2
(45) Date of Patent: Mar. 28, 2017

(54) ELECTRONIC TOOTHBRUSH

(71) Applicant: Pedram Nazeri, Ashburn, VA (US)

(72) Inventor: Pedram Nazeri, Ashburn, VA (US)

(*) Notice: Subject to any disclaimer, the term of this patent is extended or adjusted under 35 U.S.C. 154(b) by 0 days.

(21) Appl. No.: 14/788,101

(22) Filed: Jun. 30, 2015

(65) Prior Publication Data

US 2015/0374467 A1 Dec. 31, 2015

Related U.S. Application Data

(60) Provisional application No. 62/018,815, filed on Jun. 30, 2014.

(51) Int. Cl.
*A46B 15/00* (2006.01)
*A46B 17/06* (2006.01)
*A61C 17/26* (2006.01)
*A61C 19/00* (2006.01)

(52) U.S. Cl.
CPC .......... *A61C 17/26* (2013.01); *A46B 15/0034* (2013.01); *A46B 17/065* (2013.01); *A61C 19/002* (2013.01)

(58) Field of Classification Search
CPC .... A46B 15/0034; A46B 17/065; A61C 17/26
See application file for complete search history.

(56) References Cited

U.S. PATENT DOCUMENTS

| 1,671,891 A | 5/1927 | Dolan | |
| 5,476,333 A * | 12/1995 | Matthews | A46B 5/0033 |
| | | | 401/132 |
| 5,822,821 A | 10/1998 | Sham | |
| 8,584,301 B2 | 11/2013 | Maissami | |
| 9,000,398 B2 * | 4/2015 | Nelson | A61L 2/025 |
| | | | 134/18 |
| 2003/0163881 A1 | 9/2003 | Driesen et al. | |
| 2006/0016033 A1 | 1/2006 | Carpenter | |
| 2012/0124765 A1 * | 5/2012 | Lombardi | A46B 5/0041 |
| | | | 15/167.1 |
| 2014/0166900 A1 * | 6/2014 | Nelson | A61L 2/10 |
| | | | 250/455.11 |
| 2015/0143652 A1 * | 5/2015 | Walker | A46B 9/021 |
| | | | 15/160 |

FOREIGN PATENT DOCUMENTS

FR 2 721 485 * 12/1995

* cited by examiner

*Primary Examiner* — Randall Chin

(74) *Attorney, Agent, or Firm* — Global Intellectual Property Agency, LLC; Daniel Boudwin

(57) ABSTRACT

A toothbrush is provided. The toothbrush includes an elongated shaft having a brushing head removably attached thereon configured to extend and retract the brushing head from a handle portion. The handle portion is configured to support the brushing head, a rotating assembly, and an antimicrobial assembly. The rotating assembly is configured to rotatably drive the brushing head in either clockwise rotation or counterclockwise rotation. The antimicrobial assembly is configured to sterilize the brushing head and the elongated shaft shaft when retracted within the handle portion. The handle portion further includes a control panel on an exterior face of the handle portion configured to allow a user to operate the rotating assembly and/or the antimicrobial assembly. In this way, the toothbrush allows a user to achieve optimal cleaning of his teeth without introducing harmful microorganisms into his oral cavity.

11 Claims, 3 Drawing Sheets

ELECTRONIC TOOTHBRUSH

CROSS REFERENCE TO RELATED APPLICATION

This application claims the benefit of U.S. Provisional Application No. 62/018,815 filed on Jun. 30, 2014. The above identified patent application is herein incorporated by reference in its entirety to provide continuity of disclosure.

FIELD OF THE INVENTION

The present invention relates to toothbrushes. Specifically, the present invention relates to an electrical toothbrush that includes a brushing head removably attached to an elongated shaft, a rotating assembly configured to rotatably drive the brushing head, and an antimicrobial assembly configured to sterilize the brushing head.

BACKGROUND OF THE INVENTION

Generally, it is widely considered that a toothbrush is essential to maintain healthy oral hygiene. With improved technology, devices have been introduced in the prior art that provide electrical toothbrushes. These electrical toothbrushes are considered more efficient than manual toothbrushes and rapidly expanding in popularity. As a result, there are many electrical toothbrushes in the prior art with a variety of driving mechanisms and driving methods for removing plaque.

However, toothbrushes harbor microorganisms that could cause oral infection. Because the oral cavity is home to hundreds of different types of microorganisms, it is not surprising that some of these microorganisms are transferred to a toothbrush during use. Furthermore, it is also possible for these microorganisms to proliferate when transferred onto the toothbrush. Therefore, there exists a need for a toothbrush that allows a user to disinfect the toothbrush after each use.

Devices have been disclosed in the prior art that relate to electrical toothbrushes. These include devices that have been patented and published in patent application publications. Some devices provide toothbrushes with bristles that project around a spherical head. Other devices provide electrical toothbrushes having cylindrical rotatable brush heads. These devices, however, fail to provide a brushing head having a plurality of bristles thereon, whereby the brushing head is rotatably driven in either clockwise rotation or counterclockwise rotation. Furthermore, these devices also fail to provide an antimicrobial assembly that allows a user to disinfect the toothbrush after each use.

The present invention provides a toothbrush that includes a elongated shaft having a brushing head removably attached thereon configured to extend and retract from a handle portion. The handle portion forms an interior volume configured to receive and support the brushing head, a rotating assembly and an antimicrobial assembly. The rotating assembly includes an electrical motor that is configured to rotatably drive the brushing head and a battery configured to provide voltage to operate the electrical motor. The rotating assembly includes a switch that is configured to allow a user to choose between clockwise rotation and counterclockwise rotation of the brushing head. The antimicrobial assembly includes at least one UV light source configured to sterilize the brushing head and the elongated shaft. The UV light source is also connected to the battery to provide electrical power to the UV light source.

It is therefore submitted that the present invention is substantially divergent in design elements from the prior art, and consequently it is clear that there is a need in the art for an improvement to toothbrushes. In this regard, the instant invention substantially fulfills these needs.

SUMMARY OF THE INVENTION

In view of the foregoing disadvantages inherent in the known types of toothbrushes now present in the prior art, the present invention provides a toothbrush wherein the same can be utilized for allowing a user to efficiently and optimally brush their teeth without introducing harmful microorganisms into their oral cavity.

It is therefore an object of the invention to provide a new and improved toothbrush that has all of the advantages of the prior art and none of the disadvantages.

Another object of the present invention is to provide a new and improved toothbrush comprising an elongated shaft operably connected to a plurality of gears driven via a motor configured to allow for a brushing head to extend and retract from a handle portion.

Yet another object of the present invention is to provide a new and improved toothbrush, wherein the handle portion forms an interior volume configured to support the brushing head, an antimicrobial assembly, and a rotating assembly.

Still yet another object of the present invention is to provide a new and improved toothbrush, wherein the rotating assembly includes an electric motor configured to rotatably drive said brushing head and a battery configured to provide voltage to operate said electric motor.

Yet another object of the present invention is to provide a new and improved toothbrush, wherein the antimicrobial assembly includes at least one UV light source configured to sterilize the elongated shaft and the brushing head.

Another object of the present invention is to provide a new and improved toothbrush, wherein the antimicrobial assembly includes the battery configured to provide voltage to operate the UV light source.

A further object of the present invention is to provide a new and improved toothbrush, wherein the rotating assembly includes a switch configured to allow a user to choose between clockwise rotation or counter clockwise rotation of said brush head.

Yet a further object of the present invention is to provide a new and improved toothbrush further comprising a control panel on an exterior face of said handle portion.

Still yet another object of the present invention is to provide a new and improved toothbrush wherein the device may be readily fabricated from materials that permit relative economy and are commensurate with durability.

Other objects, features, and advantages of the present invention will become apparent from the following detailed description taken in conjunction with the accompanying drawings.

BRIEF DESCRIPTIONS OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 2:
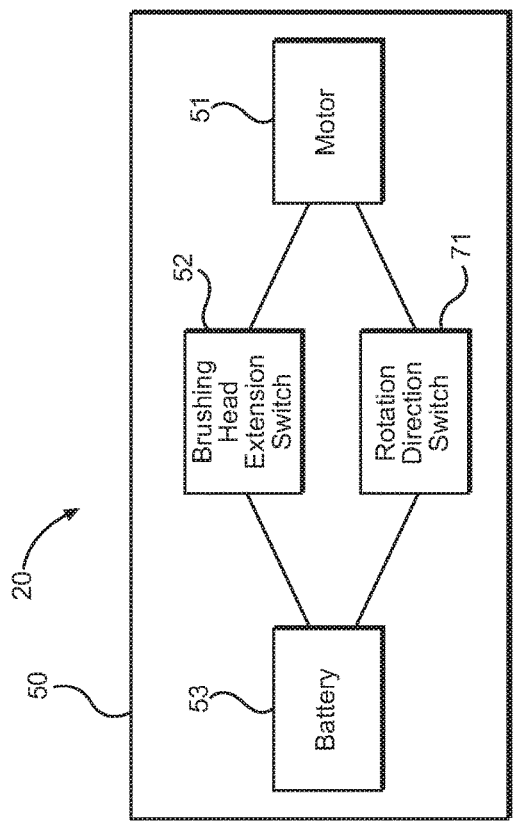
FIG. 2 shows a schematic diagram of the rotating assembly of the present invention.

Reference is made herein to the attached drawings. Like reference numerals are used throughout the drawings to depict like or similar elements of the toothbrush of the present invention. For the purposes of presenting a brief and clear description of the present invention, the preferred embodiment will be discussed as used for optimal cleaning of teeth. The figures are intended for representative purposes only and should not be considered to be limiting in any respect.

Figure 1:
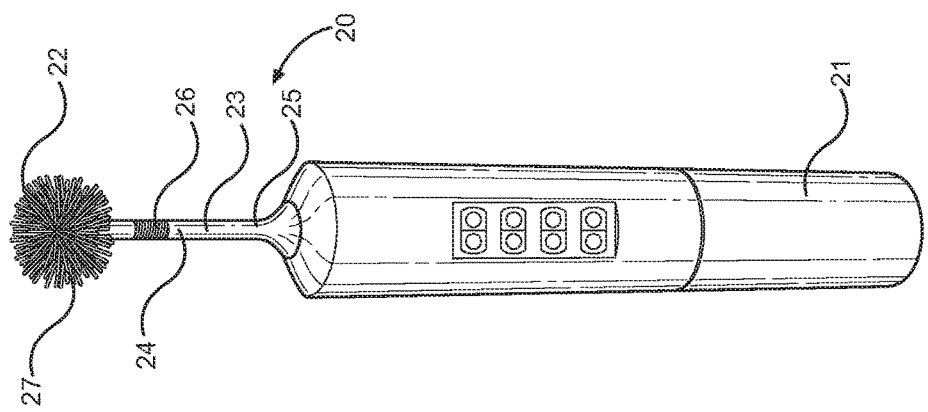
FIG. 1 shows a front perspective view of the present invention.

Referring now to FIG. 1, there is shown a front perspective of the toothbrush 20. The toothbrush 20 comprises a handle portion 21 that is configured to allow a user to grasp and maneuver the toothbrush 20. The handle portion 21 is substantially cylindrical in shape forming an interior volume in which a rotating assembly, an antimicrobial assembly and an elongated shaft 23 are positioned. The rotating assembly is configured to rotate a brushing head 22 to allow a user to better brush their teeth for cleaner and whiter teeth without reintroducing potentially harmful microorganisms into their oral cavity. The brushing head 22 is attached to the elongated shaft 23 that allows for the brushing head 22 to be received and supported within the interior volume of the handle portion 21. Furthermore, the antimicrobial assembly provides at least one UV light source that disinfects the brushing head within the interior volume of the handle portion after each use.

The elongated shaft 23 includes a proximal end 24 and a distal end 25. The proximal end 24 includes the brushing head 22 removably attached thereto via a fastener 26. Preferably, the fastener 26 includes threaded elements, however, other suitable fasteners are alternatively used in other embodiments. These variations and alterations are likewise contemplated. The distal end 25 is affixed to a plurality of gears that are driven via a motor configured to extend and retract the brushing head 22. When the brushing head 22 is not in use, a user can retract the elongated shaft 23 and the brushing head 22 to be supported within the interior volume of the handle portion 21.

Figure 4:
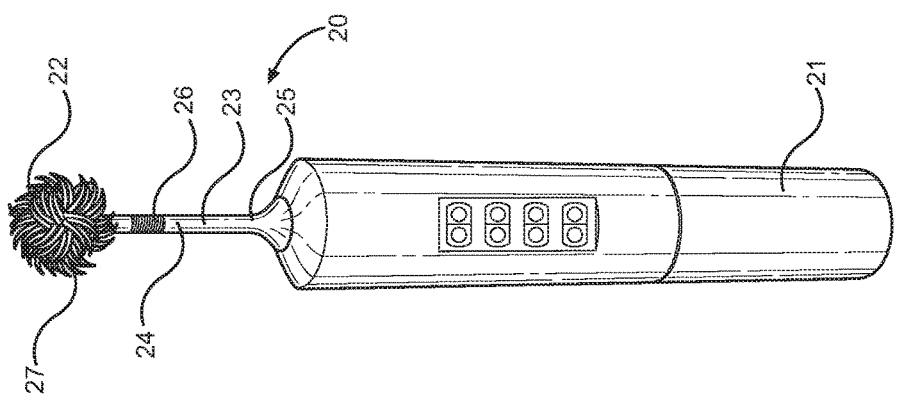
FIG. 4 shows a front perspective view of a second preferred embodiment of the present invention.

The brushing head 22 is preferably circular in shape. The brushing head 22 includes a plurality of bristles 27 that extend outwardly therefrom. As illustrated, the plurality of bristles 27 are straight bristles, however other suitable bristles are used in alternative embodiments and likewise contemplated. For example, as illustrated, in FIG. 4, there is shown a side perspective of a second preferred embodiment of the toothbrush 20. The brushing head 22 include a plurality of bristles 27 that extend outwardly therefrom. These bristles 27, however, are curved bristles. In this way, the molars of the user's teeth are cleaned more thoroughly.

Referring now to FIG. 2, there is shown a schematic diagram of the rotating assembly of the toothbrush 20. The rotating assembly 50 is configured to allow the brushing head to rotate either in clockwise or counterclockwise manner. The rotating assembly 50 that rotatably drives the brushing head includes an electric motor 51 and a battery 53 providing a source of electric power to operate the electric motor 51. Preferably, the battery 53 can be of the rechargeable type.

Further, the rotating assembly 50 includes a brushing head extension switch 52 that allows the user to extend and retract the elongated shaft 23. The brushing head extension switch 52 is electrically connected in a circuit with the electric motor 51 and the battery 53 to provide electrical power to extend and retract the elongated shaft 23. Furthermore, the rotating assembly 50 includes a rotation direction switch 71 configured to allow the user to choose between clockwise rotation and counterclockwise rotation of the brushing head.

Figure 3:
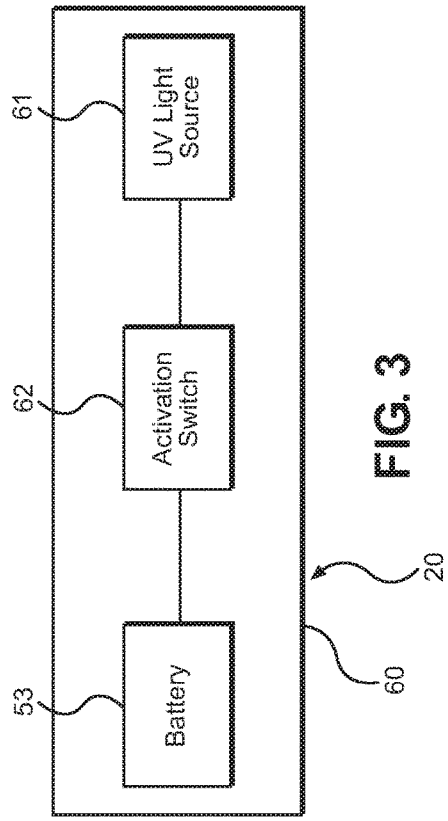
FIG. 3 shows a schematic diagram of the antimicrobial assembly of the present invention.
Figure 6:
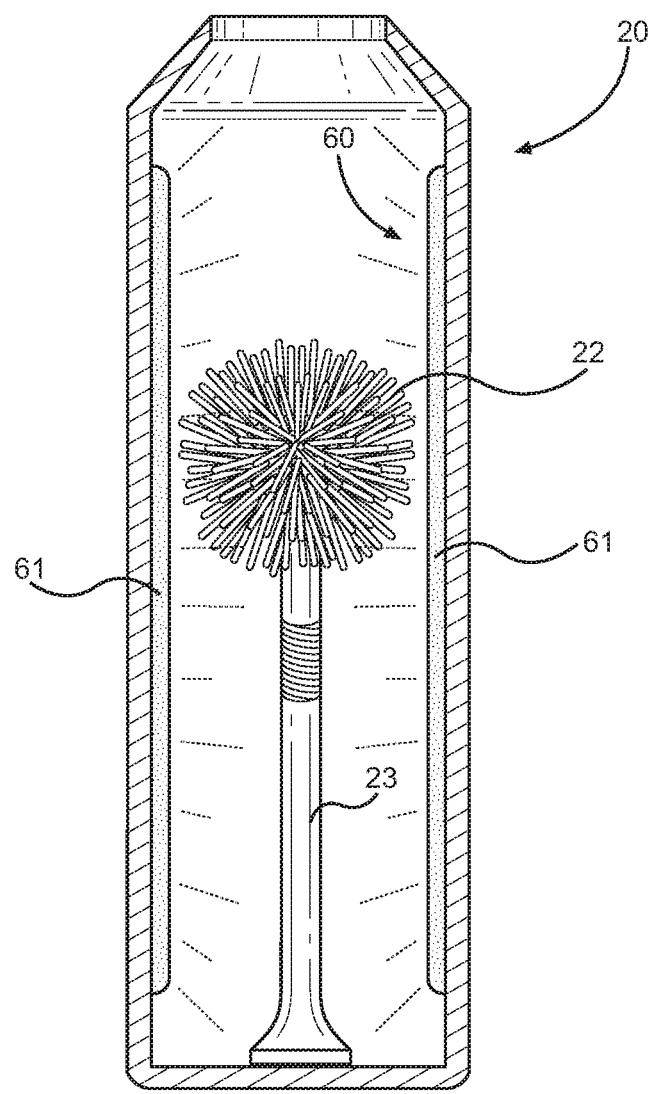
FIG. 6 shows a transparent view of the elongated shaft retracted within the handle portion of the present invention.

Referring now to FIGS. 3 and 6, there are shown a schematic diagram and a transparent view of the antimicrobial assembly of the toothbrush 20. The antimicrobial assembly 60 is supported within the interior volume of the handle portion and is configured to sterilize the elongated shaft 23 and the brushing head after each use. In this way, the moist environment of the brushing head does not promote bacteria growth and kill microorganisms, molds, and other fungi.

The antimicrobial assembly includes the battery 53, which is also configured to provide voltage to the electrical motor of the rotating assembly and at least one UV light source 61. The UV light source 61 is electrically connected to the battery 53 to provide a source of voltage to the UV light source 61. In some embodiments, the antimicrobial assembly 60 includes an indicator light that allows a user to verify that the UV light source 61 is activated. The UV light source 61 is also electrically connected to an activation switch 62 to allow the user to activate the antimicrobial assembly 60.

Figure 5:
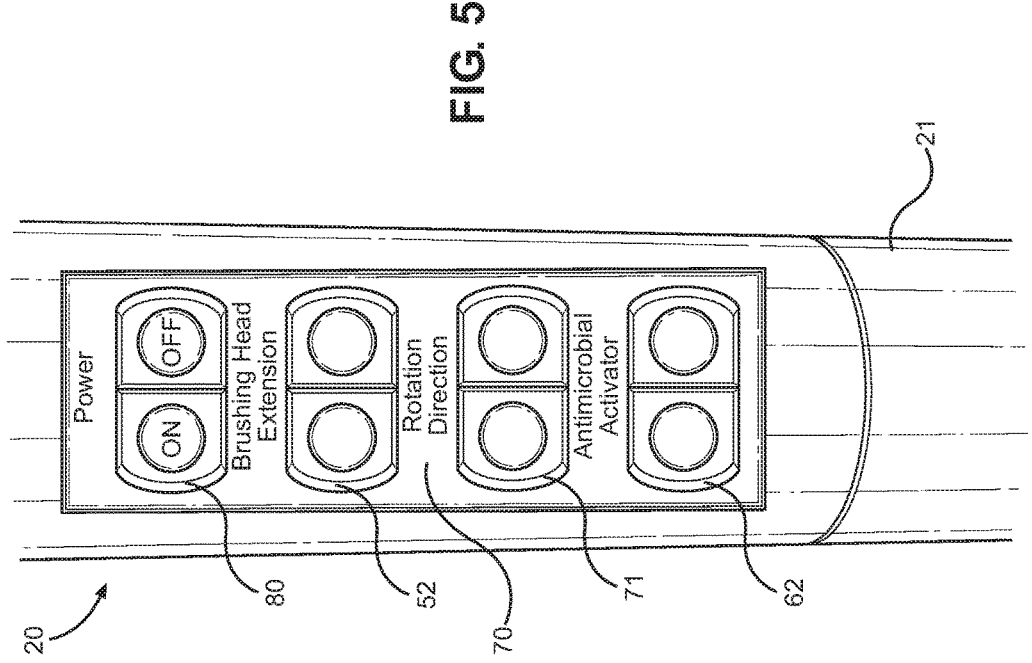
FIG. 5 shows a close-up view of the control panel of the present invention.

Referring now to FIG. 5, there is shown a front perspective of the handle portion of the toothbrush 20. The handle portion 21 of the toothbrush 20 includes a control panel 70 thereon. The control panel 70 includes one or more switches or buttons that allow the user to control the operation of the toothbrush 20. In the illustrated embodiment, the control panel 70 includes the brushing head extension switch 52 configured to extend and retract the brushing head, the activation switch 62 configured to activate the antimicrobial assembly and an on/off power switch 80 configured to provide voltage to activate the rotating assembly and/or the antimicrobial assembly. Furthermore, the control panel 70 includes a switch 71 configured to allow a user to choose between a clockwise rotation and a counterclockwise rotation for the brushing head.

It is therefore submitted that the instant invention has been shown and described in what is considered to be the most practical and preferred embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. An electronic toothbrush, comprising:
   a handle portion forming an interior volume;
   an elongated shaft extending outward from an end of said handle portion, wherein said elongated shaft is movably positioned within said handle portion such that said elongated shaft can be extended from or retracted into said handle portion;
   wherein said elongated shaft is operably connected to an electric motor at a first end thereof, and wherein said elongated shaft comprises a brushing head on a second end thereof;
   a rotating assembly configured to rotate said brushing head;
   an antimicrobial assembly disposed within said handle portion, wherein said antimicrobial assembly is adapted for use in sterilizing said brushing head;
   wherein said rotating assembly comprises: an electric motor configured to rotatably drive said brushing head either in a clockwise or counterclockwise manner; and a battery configured providing a source of electric power to operate the electric motor.

2. The toothbrush of claim 1, wherein said brushing head is circular in shape and comprises a plurality of bristles extending outwardly therefrom.

3. The toothbrush of claim 2, wherein said plurality of bristles comprises straight bristles.

4. The toothbrush of claim 2, wherein said plurality of bristles comprises curved bristles.

5. The toothbrush of claim 1, wherein said rotating assembly further comprises an activation switch configured to activate said rotating assembly.

6. The toothbrush of claim 1, wherein said rotating assembly further comprises a switch configured to allow a user to choose between clockwise rotation and counterclockwise rotation for said brushing head.

7. An electronic toothbrush, comprising:
   a handle portion forming an interior volume;
   an elongated shaft extending outward from an end of said handle portion, wherein said elongated shaft is movably positioned within said handle portion such that said elongated shaft can be extended from or retracted into said handle portion;
   wherein said elongated shaft is operably connected to an electric motor at a first end thereof, and wherein said elongated shaft comprises a brushing head on a second end thereof; a rotating assembly configured to rotate said brushing head;
   an antimicrobial assembly disposed within said handle portion, wherein said antimicrobial assembly is adapted for use in sterilizing said brushing head;
   wherein said antimicrobial assembly comprises at least one ultraviolet light source configured to sterilize the elongated shaft and the brushing head after each use within said interior volume of said handle portion.

8. The toothbrush of claim 7, wherein said antimicrobial assembly further comprises an activation switch configured to activate said antimicrobial assembly.

9. An electronic toothbrush, comprising:
   a handle portion forming an interior volume;
   an elongated shaft extending outward from an end of said handle portion, wherein said elongated shaft is movably positioned within said handle portion such that said elongated shaft can be extended from or retracted into said handle portion;
   wherein said elongated shaft is operably connected to an electric motor at a first end thereof, and wherein said elongated shaft comprises a brushing head on a second end thereof; a rotating assembly configured to rotate said brushing head;
   an antimicrobial assembly disposed within said handle portion, wherein said antimicrobial assembly is adapted for use in sterilizing said brushing head;
   wherein said handle portion comprises a control panel having one or more switches adapted to allow a user to control the operation of said brushing head.

10. The toothbrush of claim 9, wherein said control panel comprises:
    an activation switch configured to activate said antimicrobial assembly
    a brushing head extension switch configured to extend and retract said elongated shaft;
    and a rotation direction switch configured to allow a user to choose between clockwise rotation and counterclockwise rotation of said brushing head.

11. The toothbrush of claim 9, wherein said control panel further includes a power switch.

* * * * *